US008790590B1

(12) United States Patent
Wright, IV

(10) Patent No.: US 8,790,590 B1
(45) Date of Patent: Jul. 29, 2014

(54) AIR TREATMENT SUBSTANCE DELIVERY APPARATUS FOR AIR CONDITIONING SYSTEMS

(76) Inventor: Wilkinson D. Wright, IV, Pembroke Pines, FL (US)

(*) Notice: Subject to any disclaimer, the term of this patent is extended or adjusted under 35 U.S.C. 154(b) by 0 days.

(21) Appl. No.: 11/435,040

(22) Filed: May 16, 2006

Related U.S. Application Data

(60) Provisional application No. 60/681,352, filed on May 16, 2005.

(51) Int. Cl.
| | |
|---|---|
| *A61L 9/00* | (2006.01) |
| *B65D 35/22* | (2006.01) |
| *B67D 5/08* | (2006.01) |
| *B05B 1/08* | (2006.01) |

(52) U.S. Cl.
USPC .......... 422/305; 422/306; 239/73; 239/102.2; 239/310; 222/94

(58) Field of Classification Search
USPC ................. 422/1, 5, 28, 123–124, 305, 900; 239/73, 102.2, 310, 303, 328; 222/94, 222/105, 145.1
See application file for complete search history.

(56) References Cited

U.S. PATENT DOCUMENTS

| | | | | |
|---|---|---|---|---|
| 5,908,601 | A * | 6/1999 | Lin ............................... | 422/122 |
| 6,264,548 | B1 * | 7/2001 | Payne et al. ................... | 454/157 |
| 6,802,460 | B2 * | 10/2004 | Hess et al. ..................... | 239/306 |
| 6,849,234 | B2 * | 2/2005 | Lentz et al. .................... | 422/24 |
| 7,527,783 | B2 * | 5/2009 | Shaheen et al. ................ | 424/9.2 |

* cited by examiner

Primary Examiner — Monzer R Chorbaji
(74) Attorney, Agent, or Firm — Frank L. Kubler

(57) ABSTRACT

An air treatment substance delivery apparatus includes a pressurized aerosol can of air treatment substance such as a fragrance or sanitizer with a spray nozzle mounted on a conventional nozzle displacement valve, a nozzle depression mechanism actuated by a solenoid, an electric power circuit delivering power from the power source to the solenoid, the power circuit including a spray activation switch connected to air movement detection means so that activation of the air unit fan is detected by the air movement detection means which operates the spray activation switch to activate the solenoid which causes the nozzle depression mechanism to depress the spray nozzle on the can and release atomized air treatment substance into the air stream.

13 Claims, 2 Drawing Sheets

AIR TREATMENT SUBSTANCE DELIVERY APPARATUS FOR AIR CONDITIONING SYSTEMS

FILING HISTORY

This application continues from provisional application Ser. No. 60/681,352 filed on May 16, 2005.

BACKGROUND OF THE INVENTION

1. Field of the Invention

The present invention relates generally to the field of air fresheners and air fragrance and air sanitizer dispersing devices. More specifically the present invention relates to an air treatment substance delivery apparatus for placement adjacent to the air unit of a central air conditioning system to deliver atomized air treatment substance into the air unit for circulation throughout the house or other building. The air treatment substance may be, for example, a fragrance or an air sanitizer. The apparatus includes a pressurized aerosol can of air treatment substance with a spray nozzle mounted on a conventional nozzle displacement valve, a nozzle depression mechanism actuated by a solenoid, an electric power circuit delivering power from the power source to the solenoid, the power circuit including a spray activation switch connected to air movement detection means so that activation of an air unit fan is detected by the air movement detection means which operates the spray activation switch to activate the solenoid which causes the nozzle depression mechanism to depress the spray nozzle on the can and release atomized air treatment substance into the air stream. An apparatus housing preferably surrounds the aerosol can, solenoid, batteries, and most of the circuit. The apparatus housing may be mounted to a building wall inside an air intake unit closet with a housing connection structure. The air movement detection means preferably includes a fan blade mounted on a blade axle rotatably mounted to an axle mounting structure. The blade axle is connected through blade axle transmission gears to the spray activation switch, so that rotation of the blade axle, causes the switch to close, completing the spray activation circuit to deliver electric current to the solenoid, and non-rotation of the blade axle causes the switch to open the circuit and prevent electric current from reaching the solenoid. The fan blade preferably is mounted within a tubular fan shroud.

2. Description of the Prior Art

There have long been fragrance and sanitizer dispensing and atomizing devices. These generally have sprayed atomized fragrance or sanitizer substances into air only in the immediate vicinity of the device. What is needed is an air treatment substance delivery apparatus which disperses air treatment substances throughout all rooms and corridors of a building.

It is thus an object of the present invention to provide an air treatment substance delivery apparatus which is positioned adjacent the air unit of a central air conditioning system to deliver atomized air treatment substance into the air unit for delivery into central air conditioning ducts and vents so that air treatment substance is delivered throughout the building.

It is another object of the present invention to provide such an air treatment substance delivery apparatus which dispenses an air treatment substance only while the thermostat activates the central air unit, so that air treatment substance is not dispensed and wasted when the air unit is dormant.

It is still another object of the present invention to provide such an air treatment substance delivery apparatus which is readily mounted to a wall of an intake unit closet or to the air unit itself.

It is finally an object of the present invention to provide such an air treatment substance delivery apparatus which is compact and relatively inexpensive to manufacture.

SUMMARY OF THE INVENTION

The present invention accomplishes the above-stated objectives, as well as others, as may be determined by a fair reading and interpretation of the entire specification.

An air treatment substance delivery apparatus is provided for connection to an air unit having an air unit fan creating an air stream, including an air pressurized air treatment substance vessel having an air treatment substance release port in fluid communication with an air treatment substance release mechanism and an air treatment substance dispersal structure in fluid communication with the air treatment substance release mechanism; an air treatment substance release mechanism actuation mechanism; an electric power circuit containing a spray activation switch and having a power source and delivering electric current to the air treatment substance release mechanism actuation mechanism; air movement detection mechanism operationally connected to the spray activation switch; so that activation of the air unit fan is detected by the air movement detection mechanism and the air movement detection mechanism in turn operates the spray activation switch to activate the air treatment substance release mechanism, causing the air treatment substance dispersal structure release atomized air treatment substance into the air stream within the air unit.

An air treatment substance delivery system is further provided, including an air unit having an air unit fan creating an air stream; an air treatment substance delivery apparatus comprising a pressurized air treatment substance vessel having an air treatment substance release port in fluid communication with an air treatment substance release mechanism and an air treatment substance dispersal structure in fluid communication with the air treatment substance release mechanism; an air treatment substance release mechanism actuation mechanism; an electric power circuit containing a spray activation switch and having a power source and delivering electric current to the air treatment substance release mechanism actuation mechanism; air movement detection mechanism operationally connected to the spray activation switch; so that activation of the air unit fan is detected by the air movement detection mechanism and the air movement detection mechanism in turn operates the spray activation switch to activate the air treatment substance release mechanism, causing the air treatment substance dispersal structure release atomized air treatment substance into the air stream within the air unit.

An air treatment substance delivery apparatus is yet further provided for connection to an air unit having an air unit fan creating an air stream, including a pressurized aerosol can of air treatment substance with a spray nozzle mounted on a nozzle displacement release valve; a nozzle depression mechanism actuated by a solenoid; an electric power circuit delivering power from the power source to the solenoid, the power circuit comprising a spray activation switch connected to air movement detection mechanism; so that activation of the air unit fan is detected by the air movement detection mechanism, and the air movement detection mechanism operates the spray activation switch to activate the solenoid, causing the nozzle depression mechanism to depress the spray nozzle on the spray can and release atomized air treatment substance into the air stream within the air unit.

The power source preferably includes at least one battery. The air treatment substance delivery apparatus preferably additionally includes an apparatus housing surrounding the aerosol can, the solenoid, the power source, and at least part of the electric circuit. The apparatus housing preferably is mounted to a building wall inside an air intake unit closet containing the air unit with a housing connection structure. The air movement detection mechanism preferably includes a fan blade mounted on a blade axle rotatably mounted to an axle mounting structure. The blade axle preferably is connected through blade axle transmission gears to the spray activation switch; so that rotation of the blade axle causes the switch to close, completing the power circuit to deliver electric current to the solenoid, and non-rotation of the blade axle causes the switch to open the electric circuit and prevent electric current from reaching the solenoid.

The fan blade preferably is mounted within a tubular fan shroud to constrain air to flow through and rotate the fan blade. The fan shroud preferably is mounted to the apparatus housing with a shroud connection structure. A switch door preferably is connected to the shroud with a hinge switch to extend across one open end of the shroud; so that air flow adjacent the shroud bears upon and causes the switch door to pivot, causing the hinge switch to close the power circuit. The air treatment substance delivery apparatus preferably additionally includes a three-position slide switch connected to three corresponding capacitors may be provided for capacitor activation interval and duration selection. The air treatment substance preferably includes one of a fragrance and a sanitizer.

BRIEF DESCRIPTION OF THE DRAWINGS

Various other objects, advantages, and features of the invention will become apparent to those skilled in the art from the following discussion taken in conjunction with the following drawings, in which.

DETAILED DESCRIPTION OF THE PREFERRED EMBODIMENTS

Figure 1:
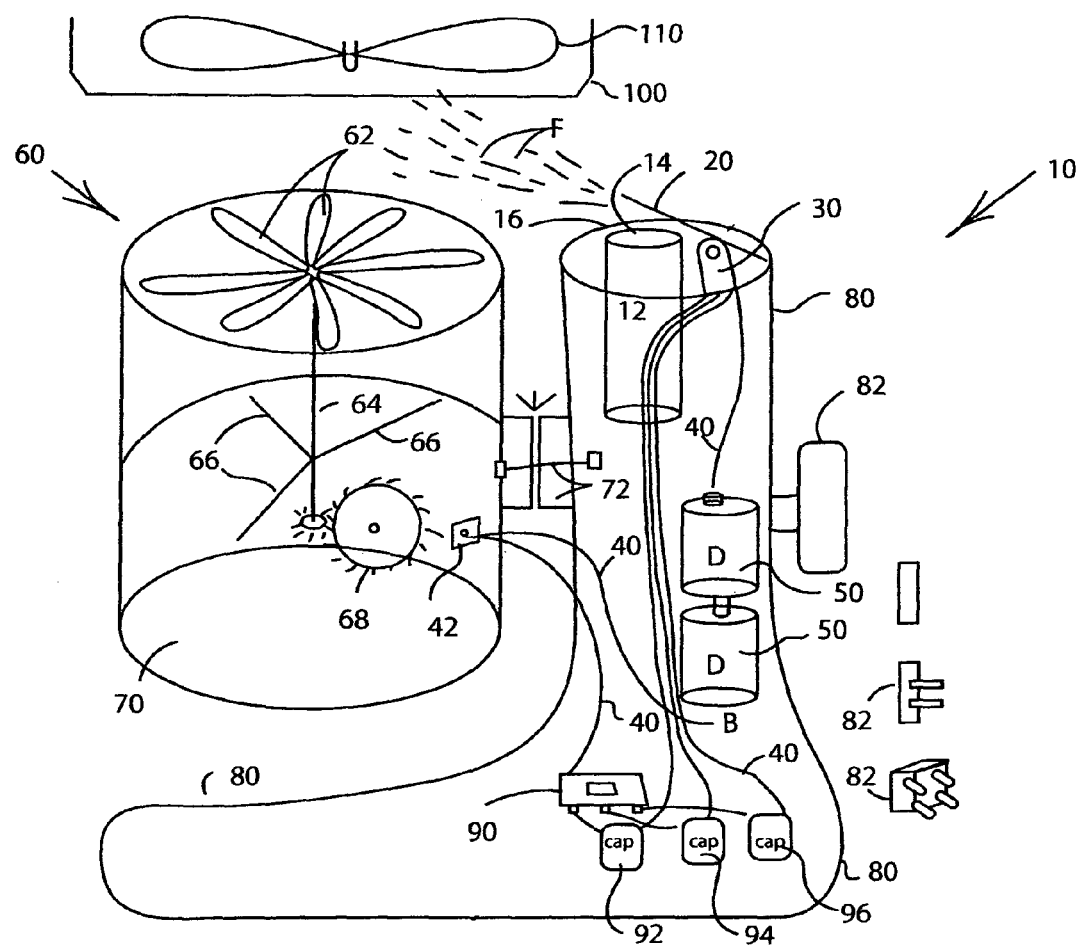
FIG. 1 is a cross-sectional perspective side view of the preferred embodiment of the air treatment substance delivery apparatus.

As required, detailed embodiments of the present invention are disclosed herein; however, it is to be understood that the disclosed embodiments are merely exemplary of the invention which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

Reference is now made to the drawings, wherein like characteristics and features of the present invention shown in the various FIGURES are designated by the same reference numerals.

First Preferred Embodiment

Figure 2:
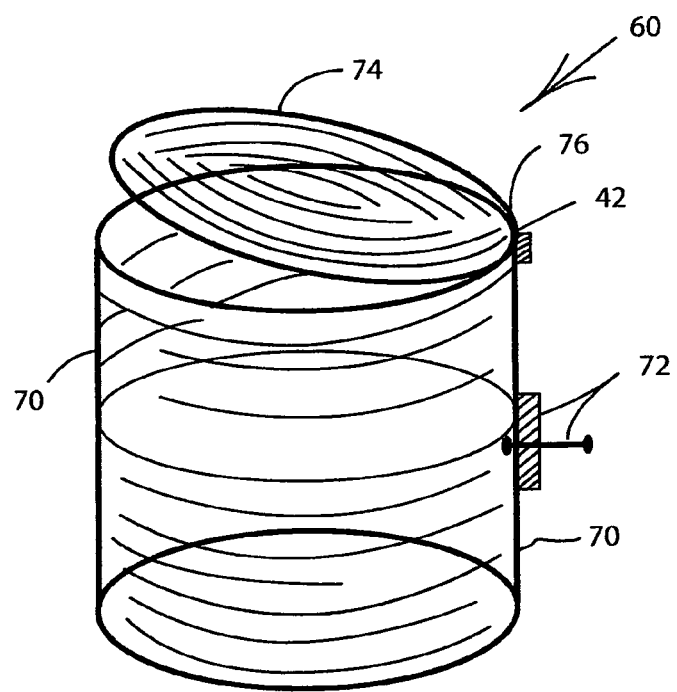
FIG. 2 is a perspective view of the alternative air movement detection means having the pivoting switch door.

Referring to FIGS. 1-2, an air treatment substance delivery apparatus 10 is disclosed for placement adjacent to the air unit 100 of a central air conditioning system to deliver atomized air treatment substance F into the air unit 100 having a unit fan 110 for circulation throughout the house or other building. Apparatus 10 may be placed in operative relation with an air intake unit or with an air output unit or other usable portion of the air unit 100. The air treatment substance F may contain an air fragrance or an air sanitizer. The apparatus 10 includes a pressurized aerosol can 12 of air treatment substance F with a spray nozzle 14 mounted on a conventional nozzle displacement valve 16, a nozzle depression mechanism 20 actuated by a solenoid 30, an electric power circuit 40 delivering power from a power source 50 to the solenoid 30, the power circuit 40 including a spray activation switch 42 connected to air movement detection means 60 so that activation of the air unit fan 110 is detected by the air movement detection means 60 which operates the spray activation switch 42 to activate the solenoid 30 which causes the nozzle depression mechanism 20 to depress the spray nozzle 14 on the can 12 and release atomized air treatment substance F into the air stream. The power source 50 preferably takes the form of two D batteries. An apparatus housing 80 preferably surrounds the aerosol can 12, solenoid 30, batteries 50, and most of the power circuit 40. The apparatus housing 80 may be mounted to a building wall W inside an air intake unit closet containing the air unit 100 with a housing connection structure 82.

The air movement detection means 60 preferably includes a detection fan blade 62 mounted on a blade axle 64 rotatably mounted to an axle mounting structure 66. The blade axle 64 is connected through blade axle transmission gears 68 to the spray activation switch 42, so that rotation of the blade axle 64, causes the switch 42 to close, completing the power circuit 40 to deliver electric current to the solenoid 30, and non-rotation of the blade axle 64 causes the switch 42 to open the circuit 40 and prevent electric current from reaching the solenoid 30. The detection fan blade 62 preferably is mounted within a tubular fan shroud 70 to help constrain unit air to flow through and rotate the detection fan blade 62. The fan shroud 70 preferably is mounted to the apparatus housing 80 with a shroud connection structure 72. As an alternative to the detection fan blade 62, a switch door 74 may be connected to the shroud 70 with a hinge switch 76 to extend across one open end of the shroud 70. See FIG. 2. Air flow adjacent the shroud 70 bears upon and causes the switch door 74 to pivot, causing the hinge switch 76 to close the power circuit 50.

The solenoid 30, and thus the spraying of air treatment substance F from the can 12, may be activated intermittently while the spray activation switch 42 is closed, at selected intervals and for selected durations. A three-position slide switch 90 connected to three corresponding capacitors 92, 94 and 96 may be provided for interval and duration selection.

The three-position slide switch 90 in the form of a microswitch permits power to generate a micro-ferred capacitor 92, electrolytic capacitor 94 or a timed latching relay circuit which then pulls down on a solenoid 30 that disperses air-fragrance, or sanitizer in the form of an air neutralizer, mold treatment, bacterial treatment, and so forth. A 24 volt AC or 12 volt DC power supply 50 is optionally provided in place of batteries for more controlled applications. A pulsing mechanism (not shown) to start apparatus 10 can be provided with a pressure switch (not shown), a temperature switch (not shown), a motion detector (not shown) or an air flap (not shown), or by hardwiring to the air unit 100 thermostat.

For the preferred embodiment, the apparatus 10 air treatment substance dispensing function is activated by rotation of the detection fan blade 62. Yet is alternatively contemplated that the apparatus 10 air treatment substance dispensing function can be activated by hardwiring the spray activation switch 42 to the air unit 100 thermostat.

An air unit 100 in some instances may not include a unit fan 110, such as in the case of a garbage shoot. Yet an air stream is still created, in this instance through the chimney effect, and this air stream is still detected by the air movement detection means 60 to activate apparatus 10.

While the invention has been described, disclosed, illustrated and shown in various terms or certain embodiments or modifications which it has assumed in practice, the scope of the invention is not intended to be, nor should it be deemed to be, limited thereby and such other modifications or embodiments as may be suggested by the teachings herein are particularly reserved especially as they fall within the breadth and scope of the claims here appended.

I claim:

1. An air treatment substance delivery apparatus for connection to a garbage chute containing an air stream, comprising:
    a pressurized aerosol can of air treatment substance with a spray nozzle mounted on a nozzle displacement release valve and positioned and oriented to release aerosol into the air stream;
    a nozzle depression mechanism actuated by a solenoid;
    an electric power circuit containing a spray activation switch and having a power source and delivering electric current to said nozzle depression mechanism;
    and air movement detection means operationally connected to said spray activation switch;
    such that air movement within the chute is detected by said air movement detection means and said air movement detection means in turn operates said spray activation switch to activate said nozzle depression mechanism, causing said air pressurized aerosol can to release atomized air treatment substance into the air stream within the garbage chute.

2. The air treatment substance delivery apparatus of claim 1, wherein said power source comprises at least one battery.

3. The air treatment substance delivery apparatus of claim 1, additionally comprising an apparatus housing surrounding said aerosol can, said solenoid, said power source, and at least part of said electric circuit.

4. The air treatment substance delivery apparatus of claim 3, wherein said fan blade is mounted within a tubular fan shroud to constrain air to flow through and rotate said fan blade.

5. The air treatment substance delivery apparatus of claim 4, wherein said fan shroud is mounted to said apparatus housing with a shroud connection structure.

6. The air treatment substance delivery apparatus of claim 1, wherein said apparatus housing is mounted to a building wall inside an air intake unit closet containing the air unit with a housing connection structure.

7. The air treatment substance delivery apparatus of claim 1, wherein said air treatment substance comprises a fragrance.

8. The air treatment substance delivery apparatus of claim 1, wherein said air treatment substance comprises a sanitizer.

9. An air treatment substance delivery apparatus for connection to a garbage chute containing an air stream, comprising:
    a pressurized aerosol can of air treatment substance with a spray nozzle mounted on a nozzle displacement release valve and positioned and oriented to release aerosol into the air stream;
    a nozzle depression mechanism actuated by a solenoid;
    an electric power circuit containing a spray activation switch and having a power source and delivering electric current to said nozzle depression mechanism;
    air movement detection means operationally connected to said spray activation switch and comprising a fan blade mounted on a blade axle rotatably mounted to an axle mounting structure;
    such that air movement within the chute is detected by said air movement detection means and said air movement detection means in turn operates said spray activation switch to activate said nozzle depression mechanism, causing said air pressurized aerosol can to release atomized air treatment substance into the air stream within the garbage chute.

10. The air treatment substance delivery apparatus of claim 9, wherein said blade axle is connected through blade axle transmission gears to said spray activation switch;
    such that rotation of said blade axle causes said switch to close, completing said power circuit to deliver electric current to said solenoid, and non-rotation of said blade axle causes said switch to open said electric circuit and prevent electric current from reaching said solenoid.

11. An air treatment substance delivery apparatus for connection to a garbage chute containing an air stream, comprising:
    a pressurized aerosol can of air treatment substance with a spray nozzle mounted on a nozzle displacement release valve and positioned and oriented to release aerosol into the air stream;
    a nozzle depression mechanism actuated by a solenoid;
    an electric power circuit containing a spray activation switch and having a power source and delivering electric current to said nozzle depression mechanism;
    air movement detection means operationally connected to said spray activation switch;
    such that air movement within the chute is detected by said air movement detection means and said air movement detection means in turn operates said spray activation switch to activate said nozzle depression mechanism, causing said air pressurized aerosol can to release atomized air treatment substance into the air stream within the garbage chute;
    and an apparatus housing surrounding said aerosol can, said solenoid, said power source, and at least part of said electric circuit;
    wherein said fan blade is mounted within a tubular fan shroud to constrain air to flow through and rotate said fan blade;
    wherein a switch door is connected to said shroud with a hinge switch to extend across one open end of said shroud;
    such that air flow adjacent said shroud bears upon and causes said switch door to pivot, causing said hinge switch to close said power circuit.

12. An air treatment substance delivery apparatus for connection to an air unit having an air unit fan creating an air stream, comprising:
    a pressurized aerosol can of air treatment substance with a spray nozzle mounted on a nozzle displacement release valve and positioned and oriented to release aerosol into the air stream;
    a nozzle depression mechanism actuated by a solenoid;
    an electric power circuit delivering power from the power source to said solenoid, said power circuit comprising a spray activation switch connected to air movement detection means;

and a multiple-position slide switch connected to a plurality of corresponding capacitors for capacitor activation interval and duration selection;

such that activation of the air unit fan is detected by said air movement detection means, and said air movement detection means operates said spray activation switch to activate said solenoid, causing said nozzle depression mechanism to depress said spray nozzle on said spray can and release atomized air treatment substance into the air stream within the air unit.

13. An air treatment substance delivery apparatus, comprising:

a pressurized air treatment substance vessel having an air treatment substance release mechanism and an air treatment substance dispersal structure for atomizing the air treatment substance in communication with said air treatment substance release mechanism;

an air treatment substance release mechanism actuation means operationally connected to said air treatment substance release mechanism for actuating said air treatment substance release mechanism;

and an electric power circuit for delivering power from a power source to said air treatment substance release mechanism actuation means, said power circuit comprising a motion detector for starting said apparatus by activating said air treatment substance release mechanism actuation means, causing said air treatment substance release mechanism to release atomized air treatment substance through said dispersal structure.

\* \* \* \* \*